United States Patent
Barth et al.

(10) Patent No.: US 7,723,261 B2
(45) Date of Patent: *May 25, 2010

(54) CATALYST FOR THE PREPARATION OF METHYL MERCAPTAN

(75) Inventors: Jan-Olaf Barth, Frankfurt (DE);
Hubert Redlingshöfer, Münchsteinach (DE); Christoph Weckbecker, Gründau-Lieblos (DE); Klaus Huthmacher, Gelnhausen (DE); Horst-Werner Zanthoff, Mülhelm a.d. Ruhr (DE); Ralf Mayer, Essen (DE)

(73) Assignee: Evonik Degussa GmbH, Essen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/102,505

(22) Filed: Apr. 14, 2008

(65) Prior Publication Data
US 2008/0262270 A1    Oct. 23, 2008

(30) Foreign Application Priority Data
Apr. 17, 2007   (EP)  ................... 07106350

(51) Int. Cl.
*B01J 23/28* (2006.01)
*B01J 23/36* (2006.01)
*C01G 39/02* (2006.01)
*C01G 47/00* (2006.01)
*C01D 1/02* (2006.01)

(52) U.S. Cl. ............... 502/321; 423/605; 423/606; 423/641

(58) Field of Classification Search .......... 502/321, 502/324; 423/593.1, 599, 605, 606, 641
See application file for complete search history.

(56) References Cited

U.S. PATENT DOCUMENTS

| 4,536,492 A | 8/1985 | Haines |
| 4,665,242 A | 5/1987 | Boulinguiez et al. |
| 2005/0040082 A1 | 2/2005 | Ogawa et al. |
| 2007/0213564 A1* | 9/2007 | Yang et al. .............. 568/70 |

(Continued)

FOREIGN PATENT DOCUMENTS

CN    1207957 A    9/1998

(Continued)

OTHER PUBLICATIONS

"Catalyst For Synthesizing Methane Thiol From Synthetic Gas Containing High-Concentration Hydrogen Sulfide", Derwent, XP002322026 (Sep. 15, 2004).

(Continued)

*Primary Examiner*—Timothy C Vanoy
*Assistant Examiner*—Daniel Berns
(74) *Attorney, Agent, or Firm*—Smith, Gambrell & Russell, LLP

(57) ABSTRACT

The present invention refers to a catalyst for the manufacture of methyl mercaptan from carbon oxides comprising Mo and K compounds and oxides or sulfides of metals chosen from the manganese group. The improvement of the present process consists of the fact that carbon dioxide can be converted with higher conversions and selectivities to methyl mercaptan as compared to state-of-the-art technologies, with only minor amounts of carbon monoxide being formed as side product. Simultaneously, carbon monoxide can be easily converted into carbon dioxide and hydrogen by reaction with water using established water-gas-shift-technologies thus increasing the overall selectivity to methyl mercaptan.

27 Claims, 2 Drawing Sheets

U.S. PATENT DOCUMENTS

2008/0293974 A1* 11/2008 Barth et al. .................. 568/70

FOREIGN PATENT DOCUMENTS

| CN | 1207958 A | 9/1998 |
| CN | 1 528 516 A | 9/2004 |
| DE | 196 54 515 C1 | 10/1998 |
| EP | 0 104 507 A1 | 4/1984 |
| EP | 0167354 A1 | 1/1986 |
| EP | 0 796 656 A1 | 9/1997 |
| EP | 0 832 878 A2 | 4/1998 |
| WO | WO 2005/040082 * | 5/2005 |

OTHER PUBLICATIONS

International Search Report and the Written Opinion—relating to International Application No. PCT/EP2008/053652 having a publication date of Oct. 23, 2008.

* cited by examiner

CATALYST FOR THE PREPARATION OF METHYL MERCAPTAN

The present invention refers to catalysts for the preparation of methyl mercaptan from carbon oxides comprising compounds of Mo, K and transition metals from the manganese group of the periodic table, especially Mn and Re.

The invention further refers to a process for the preparation of said solid catalyst system.

BACKGROUND OF THE INVENTION

Methyl mercaptan is a well known intermediate for the production of organic compounds, such as sulfur containing amino acids, pesticides and dyes. Industrially, methyl mercaptan, also known as methanethiol, is produced mainly for the synthesis of methionine, a widely used feed supplement for poultry.

Methyl mercaptan is commercially produced by the heterogeneously catalyzed gas phase reaction of methanol and hydrogen sulfide. For example, EP-B-0832878 and DE-C-19654515 disclose a methanethiol preparation method based on the reaction of hydrogen sulfide ($H_2S$) with methyl alcohol ($CH_3OH$). EP-A-167,354 discloses a synthesis pathway based on the reaction of hydrogen sulfide with carbon monoxide (CO), wherein titanium dioxide ($TiO_2$) was employed as carrier and nickel oxide (NiO) or molybdenum oxide ($MoO_3$) as active component.

Chinese Patent Applications CN 1207957 and CN 1207958 disclose a series of catalysts useful for the methanethiol synthesis from high $H_2S$-containing synthesis gas, wherein the active component (Mo—S—K-based species) comes from the precursor of $K_2MoS_4$ or $(NH_4)_2MoS_4$ plus a potassium salt. In these Chinese patent applications, dimethylformamide [$(CH_3)_2NCOH$] and not water is chosen as solvent to dissolve the active component. The described process is hard to handle and expensive.

WO2005/040082A2 refers to a continuous process for the manufacture of methyl mercaptan using Mo—O—K based catalysts and a process for the preparation of a solid, preformed catalyst system. It is further described that the total selectivity of methyl mercaptan can be increased by at least 1% by lowering the total gas hourly space velocity.

EP-A-104507 describes a continuous process for reacting carbon oxides, sulfur or hydrogen sulfide, and hydrogen at elevated pressure and temperature. The reaction is carried out over a preformed, single-phase, solid catalyst system comprising a porous alumina containing support, on which a mixture of a manganese sulfide and at least one of an iron, nickel, zinc, chromium, cobalt, molybdenum or alkali metal sulfide is deposited. The described process is a continuous, vapor-phase reaction in the presence of a specified sulfur-containing or sulfide catalyst system containing manganese to produce methyl mercaptan with improved conversions and yields. It is stated that by using the described catalyst system, the methane formation is kept to a minimum, which should result in an improved economic process. Formation of inert by-products, such as methane, should be avoided because these inert materials are difficult to separate from the recycle gases. It would build up in the recycle gas streams and would have to be vented periodically.

Other by-products of the synthesis of methyl mercaptan from carbon oxides, sulfur or hydrogen sulfide and hydrogen include carbonyl sulfide, dimethyl sulfide, carbon bisulfide and dimethyl disulfide. Especially carbonyl sulfide formation should be kept to a minimum since carbonyl sulfide is an intermediate in the formation of methyl mercaptan. Low selectivities of carbonyl sulfide result in higher selectivities of methyl mercaptan thus improving the overall yield of methyl mercaptan and the whole economy of the process.

U.S. Pat. No. 4,665,242 describes a process for the production of methyl mercaptan by heating a gas comprising carbon monoxide and/or carbon dioxide, hydrogen sulfide and hydrogen in the presence of a catalyst based on a tungsten sulfide or rhenium oxide on an activated alumina substrate. In the process, unreacted gas is recycled to the feed gas stream, wherein the water which is formed during the reaction with the catalyst, is removed from the unreacted gas. The desiccation is carried out by passing the gas through a molecular sieve. Using a $Re_2O_7/Al_2O_3$ catalyst a maximum selectivity of 64.6% at a $CO_2$-conversion of 28.0% is reported Although innumerous attempts have been started to improve the selectivity and yield of methyl mercaptan manufactured from carbon oxides there is still a need for further improvements since high selectivities of methyl mercaptan at comparatively high conversions of carbon oxides are desired. Especially, carbon dioxide as C1 source for methyl mercaptan is attractive as the major by-product carbon monoxide can be easily converted into carbon dioxide thus increasing the overall selectivity for methyl mercaptan.

Object of the Invention

It is an object of the present invention to provide a catalyst for the manufacture of methyl mercaptan from carbon oxides, preferably carbon dioxide, with high selectivities and yields for methyl mercaptan at comparatively high conversions of carbon dioxide.

SUMMARY OF THE INVENTION

The present invention is directed to a catalyst for the manufacture of methyl mercaptan by contacting an intimate mixture of carbon oxides, preferably carbon dioxide, sulfur or hydrogen sulfide and hydrogen at elevated temperatures and pressure over said catalyst comprising an oxidic or sulfidic compound of metals from the manganese group and a Mo—O—K-based active center, a promoter and a carrier.

Surprisingly, it has been found, that by using catalysts according to the invention the total selectivity of methyl mercaptan is increased to more than 80% at single pass carbon dioxide conversions of more than 50% depending on the reaction conditions chosen. It also has been found, that by using the present catalysts containing transition metals from the manganese group preferably deposited on selected $TiO_2$ carriers, for the production of methyl mercaptan from carbon dioxide the total formation of the by-product carbon monoxide can be kept to an absolute minimum. Note that carbon monoxide can be easily converted into carbon dioxide by reaction with water, so that the overall selectivity for methyl mercaptan is increased.

Furthermore, with the above mentioned catalysts, the formation of the by-products methane ($CH_4$), dimethylsulfide (DMS) and carbon bisulfide ($CS_2$) is kept to a minimum under the reaction conditions of the process described in here. This effect presents a significant advantage for the technical realization of the process, since the formation of inert gases such as methane, which have to be vented periodically, is kept to an absolute minimum. Moreover, the separation and purification of the reaction product methyl mercaptan (MC) is optimized, since only minor amounts of by-product such as carbon bisulfide, dimethylsulfide and methane are formed in the process.

Another objective of this invention is a process for preparing the solid catalyst system of the present invention.

DETAILED DESCRIPTION OF THE INVENTION

Figure 1:
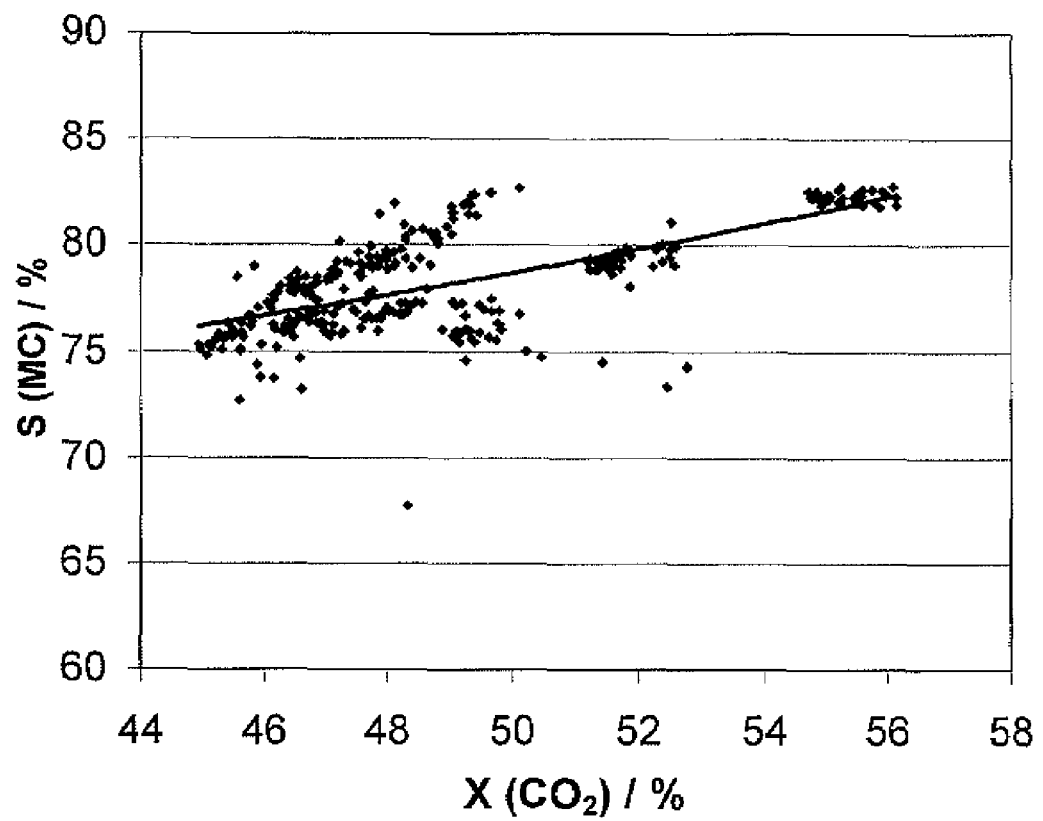
FIG. 1 is a graph showing selectivity for methyl mercaptan versus $CO_2$ conversion.

The present invention encompasses a catalyst and the method of preparing methyl mercaptan comprising contacting an intimate mixture of carbon oxides ($CO_{1-2}$), such as carbon monoxide (CO) or carbon dioxide ($CO_2$), sulfur or hydrogen sulfide, and hydrogen at elevated temperature and pressure over said solid, preformed catalyst which comprises an active component, a promoter and a carrier, and recycling the unreacted gaseous fraction to the feed gas stream in the process.

An improvement of the present process lies in the fact that carbon dioxide can be converted with higher conversion rates and selectivities to methyl mercaptan as compared to state-of-the-art technologies, with only minor amounts of carbon monoxide being formed as side product. Simultaneously, carbon monoxide can be easily converted into carbon dioxide and hydrogen by reaction with water using established water-gas-shift-technologies thus increasing the overall selectivity to methyl mercaptan.

The catalyst according to the invention comprises:

a) oxidic Mo containing and K containing compounds, whereby Mo and K can be constituents of the same compound;

b) an active oxidic compound $A_xO_y$ of elements chosen from the manganese group of the periodic table, especially Mn or Re;

c) optionally a promoter, chosen from the group of oxidic compounds $M_xO_y$ of transition metals and rare earth metals;

d) optionally $SnO_2$, instead of or additionally to $M_xO_y$.

e) an oxidic carrier or activated carbon with the exception that if alumina is used as carrier the catalyst contains a rhenium oxide or sulfide.

Mo- and K-containing compounds are preferably part of an active Mo—O—K phase located on the surface of the support material.

The invention can be also put into practice with said catalysts being treated with hydrogen sulfide. The oxidic compounds of the catalyst are then at least partially converted into sulfides or hydrosulfides.

That means that the catalytic active components of the catalyst are oxidic compounds or said sulfided compounds or mixtures of both.

The catalyst according to the invention comprises an active component consisting of oxidic or sulfidic compounds of metals of the manganese group a Mo and K compound, oxidic or sulfidic compounds or mixtures of both, a promoter and a carrier. Precursors of said manganese oxides or sulfides or rhenium oxides or sulfides are for example manganese acetate, manganese carbonate, perrhenium acid ($HReO_4$) and Dirheniumheptoxide ($Re_2O_7$). Examples of useful amounts for the purpose of the present invention are 1 to 50 wt. % $MnO_2$ or 1-50 wt. % $Re_2O_7$ of the total catalyst mass.

The weight ratios of said oxides are:

$A_xO_y/K_2MoO_4$/carrier=0.001/0.01/1-0.5/0.8/1

$A_xO_y/MoO_3/K_2O$/carrier=0.001/0.01/0.005/1-0.5/0.8/0.5/1, preferably $A_xO_y/K_2MoO_4$/carrier=0.001/0.05/1-0.3/0.5/1

$A_xO_y/MoO_3/K_2O$/carrier=0.001/0.05/0.03/1-0.3/0.5/0.3/1

Whereby A means Mn or Re and x and y are integers from 1 to 7.

A precursor of a Mo—O—K-based active center is for example, potassium molybdate ($K_2MoO_4$) or ammonium heptamolybdate $[(NH_4)_6Mo_7O_{24}] \times 4H_2O$ plus a potassium salt or $MoO_3$ plus a potassium compound. The potassium compound or salt useful in the present invention is selected from the group consisting of potassium acetate (KAc), potassium oxalate ($K_2C_2O_4$), potassium hydroxide (KOH) potassium carbonate ($K_2CO_3$), potassium nitrate ($KNO_3$), and potassium bicarbonate ($KHCO_3$). The potassium salt is solved in water and brought in calculated amounts onto the support material in general prior to or after the deposition of the remaining components of the catalyst by impregnation or coating techniques known to those skilled in the art. Examples of useful amounts of potassium salts useful for the purposes of the present invention are 1 to 50 wt. % $K_2O$, preferably 10 to 30 wt. % $K_2O$ of the total catalyst mass.

The catalyst carrier is impregnated or coated with the different catalytic components by various methods known to those skilled in the art, such as multi-step impregnation applied to the surface of the carrier or coating of the carrier with the active component. The active catalyst mass may be pressed, extruded or pelletized to produce catalysts with various three dimensional shapes and dimensions.

Additional promoters useful in the present catalyst are represented by the general formula $M_xO_y$, wherein M is selected from the group consisting of transition metals and rare-earth metals. Particularly suitable promoters are oxides of metals from the group consisting of iron (Fe), cobalt (Co), nickel (Ni), lanthanum (La) and cerium (Ce). x and y are integers from 1 to 5. The catalyst optionally contains additionally to or instead of $M_xO_y SnO_2$. Carriers useful in the present invention are preferably selected from the group consisting of silica ($SiO_2$), titanium dioxide ($TiO_2$), zeolites or activated carbon. Alumina is only used when the catalyst contains a rhenium oxide or sulfide.

When the Mo containing component is expressed by the amount of $K_2MoO_4$, the weight ratio of $K_2MoO_4/M_xO_y$/carrier equals to (0.01-0.80)/(0.01-0.1)/1, preferably (0.10-0.60)/(0.01-0.06)/1. However, when said component is expressed by the amount of $MoO_3$ and $K_2O$, the weight ratio of $MoO_3/K_2O/M_xO_y$/carrier equals to (0.10-0.50)/(0.10-0.30)/(0.01-0.10)/1, preferably (0.10-0.30)/(0.10-0.25)/(0.01-0.06)/1, respectively.

Advantageously, the support useful in the present invention is selected from the group consisting of titanium dioxide ($TiO_2$). The catalytic activity of the catalyst can be improved by using support materials with surface areas higher than 25 $m^2/g$. Advantageously, titania supports with surface areas of at least 40 $m^2/g$ and an anatase content of more than 60% are used as catalyst carriers. For practical technical purposes the high surface titanium dioxide carriers are extruded or pelletized before or after the impregnation process. Preferably, Degussa Aerolyst™ carriers or similar high-surface area titania sources are used as supports.

The shape of the support is not critical to the performance of the catalyst of the present invention and can be three dimensional spheres, cylinders, rings, stars, pellets or other three dimensional shapes or be in powder form which can be pressed, extruded or pelletized into three dimensional shapes. Advantageously, the catalyst particles have a uniform particle size distribution (standard mean deviation: 5%, characterized by particle diameters of 0.2 mm to 20.0 mm.

The present invention further relates to a process for preparing a solid, preformed catalyst system comprising the steps of I. preparing a water containing or aqueous solution comprising a manganese or rhenium containing compound, and $K_2MoO_4$ or $(NH_4)_6Mo_7O_{24}\cdot 4H_2O$ plus a potassium compound or $MoO_3$ plus a potassium compound and optionally salts of transition metals or rare earth metals; and II. impregnating a suitable carrier with said solutions followed by drying the intermediate produced, and calcinating such intermediate to obtain a catalyst; and III. optionally modification of such obtained catalyst with 1-50 wt. % $SnO_2$ by impregnation with tin containing compounds such as tri butyl tin acetate, whereby the amount of said tin compounds was chosen to reach a content of 1-50% wt. % $SnO_2$ referred.

Alternatively, the process for preparing a solid, catalyst system can be carried out according to the invention as a multi-step impregnation comprising the steps of A) preparing a water containing or aqueous solution comprising a manganese or rhenium compound and optionally a salt of a transition metal or rare-earth metal;

B) impregnating a suitable carrier with said solution, followed by drying the intermediate produced and optionally calcinating such intermediate;

C) preparing an aqueous steeping solution of $K_2MoO_4$ or $(NH_4)_6Mo_7O_{24}\cdot 4H_2O$ plus a potassium compound or $MoO_3$ plus a potassium compound; and D) steeping the intermediate produced under (B) with the aqueous solution produced under (C) and then drying and calcinating the resultant catalyst.

Optionally said catalyst is modified with 1-50 wt. % $SnO_2$ whereby said catalyst is impregnated with tin containing compounds such as tri butyl tin acetate dried, and optionally calcined.

It is also possible to change the step sequence.

An example for a preparation of a catalyst according to the present invention can be as follows:

1. A given quantity of a salt, such as nitrate, acetate or similar, of manganese or rhenium is dissolved in a given quantity of distilled water to prepare an aqueous solution, and a given quantity of the carrier chosen is impregnated for 3 to 5 hours with said solution, followed by drying at 50-130° C. for 1-3 hours to produce an intermediate. Subsequently, the resulting solid material is calcined at 300-600° C. for 5-6 h.

2. A given quantity of $K_2MoO_4$ or $(NH_4)_6Mo_7O_{24}$ plus a potassium compound or $MoO_3$ plus a potassium compound is dissolved in a given quantity of distilled water, and the intermediate prepared in step (1) is impregnated for 7-9 hours with said solution, followed by drying at 50-130° C. for 2-4 hours, and calcination at 400-500° C. for 2-4 hours.

3. The such obtained catalyst is optionally modified by suspending the catalyst in solutions of tin containing compounds such as tri butyl tin acetate and subsequent removal of the solvent to prepare a catalyst with a content of 1-50 wt. % $SnO_2$.

It is preferred to expose said catalysts to a hydrogen sulfide containing atmosphere under elevated temperature such that the oxidic compounds of the catalyst are at least partially converted to sulfidic compounds such as sulfides or hydrosulfides.

Optionally, in order to enhance the formation of the catalytic active species, the impregnation liquid and/or the steeping solution can be treated with alkyl amides, such as dimethylformamide and dimethyl acetamide, or an organic acid containing at least one carbon atom and at least one acid function. Particularly useful in the catalyst preparation process are organic acids, such as formic acid, acetic acid, propionic acid, butyric acid, pentanoic acid, hexanoic acid, acrylic acid, propiolic acid, vinylacetic acid, methacrylic acid, crotonic acid, 4-pentenoic acid, sorbonic acid, oxalic acid, malonic acid, succinic acid, maleinic acid, 3-hydroxybutyric acid, glutaric acid, adipic acid, citric acid, tartaric acid or ethylene diamine-tetracetic acid with citric acid being especially preferred.

Certain terms used herein have the following meaning with regard to the disclosure:

The term "active catalyst mass" means a composition of a catalyst support (carrier) impregnated or coated with various mixed oxides representing the catalytically active species.

The term "catalytically active components" means the oxides or sulfides or hydrogen sulfides of the metals which are present on the surface of the carrier after being impregnated or covered with compounds of said metals.

The terms "support" and "carrier" are used concurrently with the same meaning. The terms denote porous materials which have various three dimensional forms and dimensions and which provide a high specific surface area.

The term "single-phase" solid catalyst means a catalytically active mass of intimately mixed components which are solid materials and which are optionally impregnated or deposited on a support or carrier material.

The term "promoter" means the transition metal oxide or hydroxide or transition metal sulfide or hydrosulfide or transition metal salt precursor prior to or after sulfiding.

The term "sulfide" as used herein means a material including simple sulfides and hydrosulfides and complex sulfides.

The term "sulfiding" or "sulfided" as used herein relates to the treatment of the active catalyst mass with hydrogen sulfide or vaporous or liquid elemental sulfur and hydrogen under elevated temperature for a time such that the active components of the catalyst are at least partially converted to the sulfide. Conversion of the catalytically active species from the oxide, hydroxide or any other salt to the sulfide state will change the weight of the compound somehow. Nevertheless, it will permit, prior to sulfiding, the use of the sulfide precursor within the same weight range as described herein for the sulfide in order to provide a catalyst system as defined for this invention.

The term "(gas hourly) space velocity" as used herein, refers to the total volume (usually in liters) of carbon oxides, hydrogen and hydrogen sulfide passing through a unit volume (usually 1 liter) of the catalyst system during one hour measured at a standard temperature and pressure.

The term "yield" denotes the number of moles of CO or $CO_2$ per initial 100 moles actually converted into methyl mercaptan or any other specified by-product.

As used herein, the term "conversion" indicates the percentage of the moles of carbon dioxide that were converted to methyl mercaptan or any other reaction product, The part percentage which gives rise to methyl mercaptan alone is called selectivity.

Thus, Yield=Conversion×Selectivity

Carbon dioxide, hydrogen sulfide or elemental sulfur and hydrogen are the preferred starting materials for the process of the present invention. Carbon monoxide may be used to replace part or all of the carbon dioxide, but it has been found that carbon dioxide provides higher selectivities for methyl mercaptan than carbon monoxide.

Mixtures of carbon monoxide and hydrogen in various stoichiometric ratios are also known as synthesis gas and are easily produced by various methods, such as partial oxidation of hydrocarbons, steam reforming of natural gas, naphtha and high vacuum residues from crude oil distillation or coal gasification. The well known process of steam reforming of natural gas (methane) can be exemplified according to the equation:

$$CH_4 + H_2O \rightarrow CO + 3H_2 \quad \text{(Equ. 1)}$$

By addition of water carbon monoxide is converted to carbon dioxide and hydrogen as exemplified by equation 2. Note that the total $CO_2/H_2$ ratio is 1/4 (Equ. 3) making it an ideal feed gas for the synthesis of methyl mercaptan from carbon dioxide, hydrogen and sulfur (Equ. 7).

$$CO + H_2O \rightarrow CO_2 + H_2 \quad \text{(Equ. 2)}$$

$$CH_4 + 2H_2O \rightarrow CO_2 + 4H_2 \quad \text{(Equ. 3)}$$

Hydrogen sulfide may be supplied to the process or it may be formed in situ in the process by reacting elemental sulfur in the molten or vapor state either before, during or after contacting them with the feed of reactants in the reactor. Elemental sulfur may be fed together with carbon oxides and hydrogen directly to the reactor, since under the temperature and pressure conditions of the present invention, sulfur will be in the molten state and will form $H_2S$ immediately upon contact with hydrogen. The chemical reactions can be exemplified as:

$$CO + H_2S + 2H_2 \rightarrow CH_3SH + H_2O \quad \text{(Equ. 4)}$$

$$CO_2 + H_2S + 3H_2 \rightarrow CH_3SH + 2H_2O \quad \text{(Equ. 5)}$$

$$CO + S + 3H_2 \rightarrow CH_3SH + H_2O \quad \text{(Equ. 6)}$$

$$CO_2 + S + 4H_2 \rightarrow CH_3SH + 2H_2O \quad \text{(Equ. 7)}$$

It is believed that, over the catalysts described herein, the reaction proceeds via the hydrogenation of the intermediate carbonyl sulfide (COS) which is formed upon the reaction of carbon monoxide or carbon dioxide and hydrogen sulfide:

$$CO + H_2S \rightarrow COS + H_2 \quad \text{(Equ. 8)}$$

$$CO_2 + H_2S \rightarrow COS + H_2O \quad \text{(Equ. 9)}$$

$$COS + 3H_2 \rightarrow CH_3SH + H_2O \quad \text{(Equ. 10)}$$

For the process described herein, it has been found, that, by using the present catalysts, the yield of the intermediate carbonyl sulfide can be minimized by employing catalysts containing transition metals of the manganese group thus resulting in increased yields of methyl mercaptan. Preferably rhenium containing compounds are employed showing high selectivities for methyl mercaptan at high conversions of carbon dioxide.

Furthermore, by using the catalysts described herein, it has been found that the formation of methanol and dimethylether as reaction products of carbon oxides with hydrogen does not occur within the temperature and pressure range described herein. Consequently, using carbon dioxide as carbon source, only carbon monoxide, methane, carbonyl sulfide, carbon bisulfide, and dimethylsulfide are the only potential reaction by-products accompanied by trace amounts of higher (poly) sulfides and hydrocarbons formed by Fischer-Tropsch type reactions.

The feed rate of the reactants through the catalyst bed of the reactor is reported herein as total gas hourly space velocity. The reaction of the present invention can be operated at space velocities in the range of 1 to 10000 $h^{-1}$, preferably of from 100 to 5000 $h^{-1}$ and more preferably of from 300 to 3000 $h^{-1}$. The optimum space velocity employed will vary between 450 and 3000 $h^{-1}$ depending upon the other conditions of the process, such as temperature, pressure and molar ratio of the reactants. It has been found, that the lower the space velocity the higher the selectivity for methyl mercaptan and the lower the formation of undesired by-products, such as carbonyl sulfide and methane.

The molar ratio of reactants in the feed mixture, i.e., carbon oxide, hydrogen sulfide or elemental sulfur and hydrogen should be chosen so as to result in an excess of hydrogen sulfide. Preferably, the molar ratios of $CO_{1-2}/H_2S/H_2$ reaches from 1/1/0 and 1/8/8, preferably from 1/2/1 to 1/4/4. When utilizing elemental sulfur to replace $H_2S$ in the feed, the molar ratio of the reactants $CO_{1-2}/S/H_2S/H_2$ will preferably reaches from 1/1/0/1 and 1/8/8/8, more preferably from /2/2/1 to 1/4/4/4. As shown in the equation below, the presence of hydrogen is not a prerequisite for the formation of methyl mercaptan. With the process and catalysts of the present invention, methyl mercaptan can be readily formed by using $H_2S$ as sulfur source in the absence of hydrogen.

$$3CO + 2H_2S \rightarrow CH_3SH + COS + CO_2 \quad \text{(Equ. 11)}$$

It is advantageous to carry out the present process using a series of fixed catalyst beds or a reactor comprising one or multiple (n=1-10) reaction zones for the chemical reaction, in which one or more of the reacting gases can be fed between the reaction zones. The catalyst may be arranged in fixed beds with intermediate gas injection or multitubular reactors for a better temperature control.

According to a preferred embodiment of the process of this invention, the reactants carbon oxide, sulfur, hydrogen sulfide and hydrogen are mixed in the desired molar ratio before being fed to the reactor. The reactants may be introduced separately at different zones/catalysts beds which are sequentially arranged in the reactor to increase the overall yield of methyl mercaptan. Preferably, hydrogen and/or hydrogen sulfide are introduced between the catalyst beds, thus increasing the overall yield of methyl mercaptan.

The reactants are advantageously preheated to at least 120° C. prior to entering the reactor. The preferred preheating temperature ranges from 120 to 350° C. Using elemental sulfur as sulfur source, the reacting gases may be either fed through liquid sulfur at temperatures preferably between 140 and 450° C. or they may be mixed with gaseous sulfur prior to entering the reactor.

The temperature in the reactor is generally controlled by the temperature of the catalyst bed which ranges from at least 200° C. to up to 500° C., preferably between 250 and 400° C., more preferably between 220 and 350° C. When sulfur is used as reactant in the process, the temperature and pressure in the reactor should be at least sufficient to maintain sulfur in the liquid state. Although the reaction is exothermic, further heat is supplied externally.

It has been found that, in the present process, the formation of the by-product carbon monoxide can be minimized by gradually increasing the reaction temperature and consequently the conversion of carbon dioxide. This effect is interesting since usually the formation of by-products is supported by increasing the reaction temperature. The pressure in the reactor is generally above 5 bar, preferably >10. To increase the yield of methyl mercaptan the pressure is preferably within the range of 15-50 bar, more preferably in the range of 20-40 bar.

Prior to starting the reaction, the catalysts are preconditioned in a flow of hydrogen sulfide or hydrogen sulfide, hydrogen and carbon dioxide at temperatures between 20 and 500° C., preferably between 200 and 400° C., and pressures between 1 and 50 bar. Subsequently, the catalysts are exposed to a flow of hydrogen sulfide or hydrogen and elemental sulfur and carbon dioxide under reaction conditions. The total time for the preconditioning process may range from 1 hour (h) to 48 hours, preferably of from 2 to 24 h.

The present invention is explained in more detail in the following with the aid of embodiment examples.

EXAMPLE 1

Preparation of the Catalysts A Through E

Catalyst A

An aqueous solution of 2.0635 g of perrhenium acid ($HReO_4$) dissolved in 20 ml of distilled water was prepared. 50 g of $TiO_2$-support were impregnated with 18 ml of this $HReO_4$-solution under continuous stirring. The impregnated support was agitated for 5 min followed by aging for 30 min at room temperature. Subsequently, the material was dried in an oven at 100° C. for 4.5 h. An aqueous solution of 23.73 g of potassium molybdate dissolved in 25 ml of distilled water was prepared. The impregnated support was coated with 18 ml of the $K_2MoO_4$-solution. The second impregnation was performed analogously to the first impregnation-step. After aging for 30 min at room temperature the catalyst was dried in an oven at 100° C. for 2 h, followed by calcination at 500° C. (1 h).

Catalyst B

An ethanolic solution of 0.5882 g tributyl tin acetate dissolved in 31.9 g of ethanol was prepared. 19.8 g of catalyst A were impregnated with the solution at 50° C. for 1.5 h under continuous rotation. Subsequently, ethanol was removed under vacuum followed by calcination for 2 h at 150° C.

Catalyst C

An aqueous solution of 4.291 g of manganese acetate× $4H_2O$ dissolved in 20 ml of distilled water was prepared. 50 g of $TiO_2$-support were coated with 18 ml of this Mn-acetate-solution under continuous rotation. The impregnated support was agitated for 5 min and left for aging for 30 min at room temperature followed by drying in an oven at 100° C. for 4.5 h. An aqueous solution of 23.73 g of potassium molybdate dissolved in 25 ml of distilled water was prepared. The impregnated support was coated with 18 ml of the $K_2MoO_4$-solution. After aging for 30 min at room temperature the catalyst was dried in an oven at 100° C. for 2 h, followed by calcination at 500° C. for 1 h.

Catalyst D 31.7 g of $K_2MoO_4$, were dissolved under stirring in 65 ml of distilled water (pH ~9.5-10). 26.7 g of citric acid were added in portions to the solution. Subsequently, 10.7 g of manganese acetate were added and dissolved. The impregnation liquid (pH ~5.5) was brought into contact with 75 g of $TiO_2$-support which was impregnated for 24 h then filtered, dried at room temperature. Finally, the catalyst was dried in an oven at 80° C. for 2 h, and calcined at 500° C. for 1 h.

Catalyst E

A 5% solution of manganese acetate in distilled water was prepared. 50 g of □-$Al_2O_3$ support material suspended in distilled water were added in portions of 10 ml under continuous agitation to this impregnation solution. Subsequently, the suspension was agitated for 5 min and left for aging for 30 min at room temperature. The catalyst was dried at room temperature for 1 day followed by drying in an oven at 100° C. for 2 h. An aqueous solution of cesium hydroxide was prepared. The impregnated support was coated with the CsOH-solution. After aging for 30 min at room temperature the catalyst was dried in an oven at 80° C. for 2 h, cooled down to room temperature followed by calcination at 500° C. (1 h) to produce a catalyst with a loading of 19 m % $MnO_2$ and 10 m % CsOH.

EXAMPLE 2

The catalysts A-E described in Example 1 were tested under the following reaction conditions: the total gas hourly space velocity was 750-3000 $h^{-1}$, the reactant molar ratio for $CO_2/H_2/H_2S$ was 1/4/4, respectively and the catalyst bed temperature was 250-350° C. (maximum) and the absolute pressure was 30 bar. The catalytic activity was evaluated for a single-pass of the reactor. Determination of conversions and selectivities were made as described above.

TABLE 1

| Catalyst | Carrier | Conversion ($CO_2$)/% | Selectivity (MC)/ | Selectivity (CO)/% | Selectivity ($CH_4$ or COS)/% |
|---|---|---|---|---|---|
| Catalyst A $Re_2O_7$/ $K_2MoO_4/TiO_2$ | $TiO_2$ | 55.8 | 82.2 | 11.8 | 4.5 ($CH_4$) |
| Catalyst B $SnO_2$/ $Re_2O_7$/ $K_2MoO_4/TiO_2$ | $TiO_2$ | 53.5 | 82.6 | 9.9 | 4.8 ($CH_4$) |
| Catalyst C $Mn_xO_y$/ $K_2MoO_4/TiO_2$ | $TiO_2$ | 50.1 | 81.5 | 12.6 | 3.5 ($CH_4$) |
| Catalyst D $Mn_xO_y$/ $K_2MoO_4/TiO_2$ | $TiO_2$ | 48.5 | 80.4 | 13.9 | 3.4 ($CH_4$) |
| Catalyst E $MnO_2$/ $CsOH/Al_2O_3$ | $Al_2O_3$ | 33 | 3.8 | 81.4 | 14.5 (COS) |

$CO_2$ = carbon dioxide
MC = methyl mercaptan

EXAMPLE 3

Table 2 shows the catalytic activity of a catalyst consisting of $SnO_2$—$Re_2O_7$—$K_2MoO_4$-$TiO_2$ impregnated on a Degussa Aerolyst $TiO_2$ carrier with a loading of 1 wt % $SnO_2$ as compared to a state-of-the-art $Re_2O_7$—$Al_2O_3$ catalyst. The materials were tested under the following reaction conditions: the total gas hourly space velocity was 400-3000 $h^{-1}$, the reactant molar ratio for $CO_2/H_2/H_2S$ was 1/4/4, respectively, the catalyst bed temperature was 250-400° C. and the absolute pressure was 30 bar. The catalytic activity was evaluated for a single-pass of the reactor. Determination of conversions and selectivities were made as described above. Note the reduced formation of carbon monoxide and methane accompanied by significantly increased selectivities and yields of methyl mercaptan as compared to a $Re_2O_7$ catalyst impregnated on $Al_2O_3$-support material.

TABLE 2

| Catalyst | Conversion ($CO_2$)/% | Yield (MC)/% | Selectivity (MC)/% | Selectivity (CO)/% | Selectivity ($CH_4$)/% |
|---|---|---|---|---|---|
| 1 wt % $SnO_2$—$Re_2O_7$—$K_2MoO_4$—$TiO_2$ | 53.5 | 44.2 | 82.6 | 9.9 | 4.8 |
| 3.25% $Re_2O_7$/$Al_2O_3$ | 28.0 | 18.1 | 64.6 | 25.2 | 7.9 |

EXAMPLE 4

Figure 2:
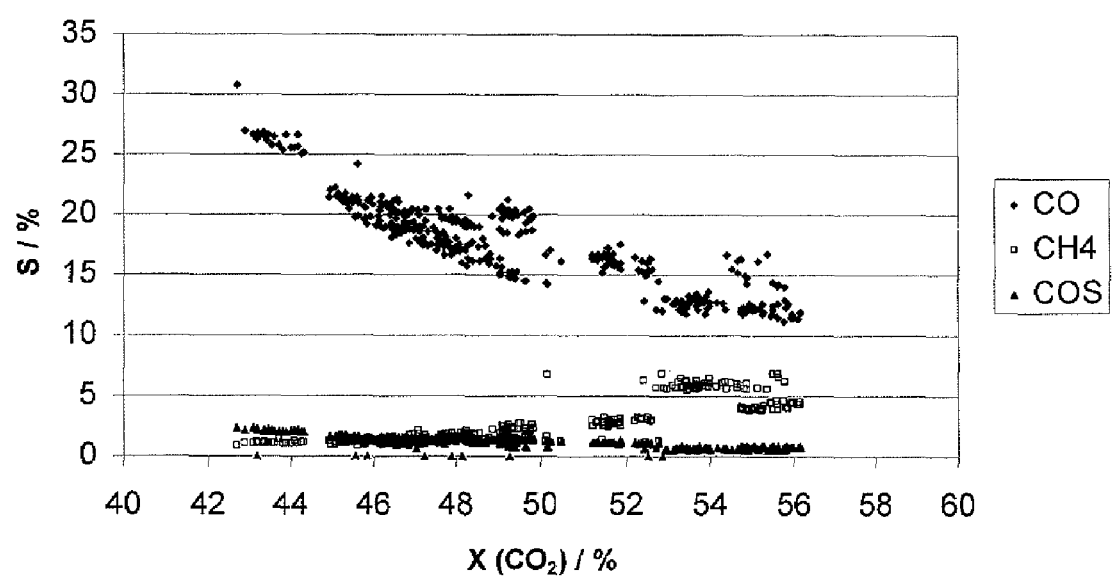
FIG. 2 is a graph showing increased selectivity for methyl mercaptan versus $CO_2$ conversion.

Catalyst A was tested under the following reaction conditions: the total gas hourly space velocity was 750 $h^{-1}$-3000 $h^{-1}$, the reactant molar ratio for $CO_2/H_2/H_2S$ was 1/4/4, the catalyst bed temperature was varied between 220° C. (minimum) and 340° C. (maximum) and the absolute pressure was 30 bar. The catalytic activity was evaluated for a single-pass of the reactor. FIGS. 1 and 2 show the selectivity for methyl mercaptan and side product formation as a function of $CO_2$ conversion.

FIG. 2 demonstrates that the formation of the by-products carbon monoxide is minimized by increasing the conversion of carbon dioxide accompanied by increased selectivities for methyl mercaptan GHSV=gas hourly space velocity S=selectivity

The invention claimed is:

1. Supported catalyst comprising:
    a) oxidic Mo containing and K containing compounds, consisting of: $K_2MoO_4$ or $MoO_3$ and $K_2O$;
    b) an active oxidic compound $A_xO_y$, wherein A represents Re and x and y are integers from 1 to 7; and
    c) a carrier.

2. The catalyst according to claim 1, further comprising a promoter, selected from the group consisting of oxidic compounds of the formula $M_xO_y$ of transition metals and rare earth metals, wherein x and y are integers from 1 to 7 according to the oxidation level of the metals and M means a transition or rare earth metal.

3. The catalyst according to claim 2, wherein the transition or rare earth metal is selected from the group consisting of Fe, Co, Ni, La, and Ce.

4. The catalyst according to claim 1, wherein weight ratios of components are $K_2MoO_4/M_xO_y$/carrier=(0.01-0.80)/(0.01-0.1)/1

$MoO_3/K_2O/M_xO_y$/carrier=(0.10-0.50)/(0.10-0.30)/(0.01-0.1)/1 wherein x and y are integers from 1 to 7.

5. The catalyst according to claim 4, wherein weight ratios of components are $K_2MoO_4/M_xO_y$/carrier=(0.10-0.60)/(0.01-0.06)/1

$MoO_3/K_2O/M_xO_y$/carrier=(0.10-0.30)/0.10-0.25)/0.01-0.06)/1.

6. The catalyst according to claim 2, wherein M is a metal selected from the group consisting of iron, cobalt, nickel, lanthanum and cerium.

7. The catalyst according to claim 2, wherein M of the formula $M_xO_y$ means tin instead of or additionally to said rare earth or transition metals.

8. The catalyst according to claim 1, comprising oxidic and/or sulfided compounds of Mo, K, elements A and M, achievable by treating oxidic compounds of said elements with hydrogen sulfide.

9. The catalyst according to claim 1, wherein the carrier is selected from the group consisting of silica, titanium dioxide, zeolites and activated carbon.

10. The catalyst according to claim 1, wherein the carrier is alumina and the catalyst contains a rhenium oxide or rhenium sulfide.

11. The catalyst according to claim 9, wherein the carrier is a titanium dioxide containing at least 60% anatas.

12. A method to prepare a catalyst according to claim 1, comprising the steps:
    a) impregnating a carrier in one or more steps with an aqueous solution comprising a compound of metal from the manganese group, a K containing compound which acts as a $K_2O$ precursor and $(NH_4)_6Mo_7O_{24}.4H_2O$ or $MoO_3$ containing compound; or
    b) impregnating said carrier in one or more steps with one or more aqueous solutions comprising a compound of metal from the manganese group, and $K_2MoO_4$; and
    c) drying said carrier impregnated thereby.

13. A method according to claim 12, wherein the carrier is additionally impregnated with an aqueous solution of a metal compound selected from the group consisting of transition metals and rare earth metals.

14. A method according to claim 13, wherein the metal is selected from the group consisting of Fe, Co, Ni, La and Ce.

15. A method according to claim 12, wherein the carrier is impregnated with a solution of a tin compound which acts as a precursor of $SnO_2$.

16. A method according to claim 13, wherein nanodisperse $CeO_2$ is suspended in one of the solutions used for impregnating the carrier.

17. A method according to claim 12, wherein a solution used for impregnation contains an alkyl amide, or an organic acid containing at least one carbon atom and at least one acid function.

18. A process according to claim 17, wherein the alkyl amide is dimethylformamide or dimethyl acetamide, and the acid function is an organic and selected from the group consisting of formic acid, acetic acid, propionic acid, butyric acid, pentanoic acid, hexanoic acid, acrylic acid, propiolic acid, vinylacetic acid, methycrylic acid, crotonic acid, 4-pentoenoic acid, sorbonic acid, oxalic acid, malonic acid, succinic acid, maleinic acid, 3-hydroxybutyric acid, glutaric acid, adipic acid, citric acid, tartaric acid and ethylene diamine-tetracetic acid.

19. A process according to claim 18, wherein the organic acid is citric acid.

20. A method according to claims 11, wherein the dried and optionally calcined catalyst is exposed to a hydrogen sulfide containing atmosphere of elevated temperatures.

21. A method for preparing methyl mercaptan in a catalytic reaction process comprising reacting carbon oxides, sulphur and/or hydrogen suiphide, and hydrogen, optionally water as reactants, in the presence of a supported catalyst according to claim 1.

22. The method according to claim 21, wherein the reactants are used in molar ratios of $CO_{1-2}/H_2S/H_2$ ranging from 1/1/0 to 1/8/8, or when utilizing elemental sulfur to replace $H_2S$ in the feed, the molar ratio of the reactants $CO_{1-2}/S/H_2S/H_2$ ranges between 1/1/0/1 and 1/8/8/8.

23. The method according to claim 22, wherein the molar ratios of $CO_{1-2}/H_2S/H_2$ reaches from 1/2/1 to 1/4/4, or when utilizing elemental sulfur to replace $H_2S$ in the feed, the molar ratio of the reactants $CO_{1-2}/S/H_2S/H_2$ ranges from 1/2/2/1 to 1/4/4/4.

24. The method according to claim 22, wherein $CO_2$ is used as carbon oxide.

25. The method according to claim 21, wherein the reacting takes place at a temperature is in the range of 200-500° C. and the pressure from 5 to 50 bara.

26. The method according to claim 21, wherein the reaction is performed in a tubular, multi tubular, fixed bed, catalytic wall micro channel or fluidized bed reactor.

27. The method according to claim 21, wherein a gas hourly space velocity of 1-10000 $h^{-1}$ is applied.

* * * * *